United States Patent
Lammert et al.

(10) Patent No.: US 8,191,796 B2
(45) Date of Patent: Jun. 5, 2012

(54) FRAGRANCE DISPENSER

(75) Inventors: Matthias Lammert, Atizapán de Zaragoza (MX); Alma Ortiz Vela, Cuautitlan Izcalli (MX); Angelica Leal Mendieta, Cuautitlan Izcalli (MX); Maria De la Luz Hernandez Sanchez, Naucalpan de Juarez (MX); Ruben Israel Chavez Rico, Cuautitlan Izcalli (MX); Carlos Eloy Embarcadero Dominguez, Cuautitlan Izcalli (MX)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 12/528,006

(22) PCT Filed: Feb. 28, 2007

(86) PCT No.: PCT/EP2007/051912
§ 371 (c)(1),
(2), (4) Date: Nov. 10, 2009

(87) PCT Pub. No.: WO2008/104226
PCT Pub. Date: Sep. 4, 2008

(65) Prior Publication Data
US 2010/0056422 A1    Mar. 4, 2010

(51) Int. Cl.
*A61K 8/00* (2006.01)
*A61K 8/18* (2006.01)
*A24F 25/00* (2006.01)
*A61L 9/04* (2006.01)
*B05B 15/00* (2006.01)
*B05B 17/00* (2006.01)
*A62C 13/62* (2006.01)
*A62C 13/66* (2006.01)
*A61L 9/00* (2006.01)

(52) U.S. Cl. ......... 239/57; 512/1; 512/2; 512/8; 512/25; 512/26; 512/27; 239/6; 239/8; 239/44; 239/54; 239/56; 239/34; 239/289; 239/303; 239/308; 424/76.2; 422/5

(58) Field of Classification Search ........... 512/1, 2, 512/8, 20, 25, 26, 27; 239/6, 8, 34, 44, 54, 239/56, 57, 58, 60, 76, 289, 303, 308; 510/109, 510/403, 513; 362/643; 424/76.2; 454/100; 568/300, 420, 425; 556/437; 422/5
See application file for complete search history.

(56) References Cited

U.S. PATENT DOCUMENTS 3,685,734 A    8/1972   Paciorek et al.
(Continued)

FOREIGN PATENT DOCUMENTS
EP         0348970 A2      1/1990
(Continued)

OTHER PUBLICATIONS

Webster's Ninth Collegiate Dictionary (Merriam-Webster Inc. 1985 gel: col. 1 p. 509).*
(Continued)

*Primary Examiner* — Patrick Ryan
*Assistant Examiner* — Aaron Greso
(74) *Attorney, Agent, or Firm* — Connolly Bove Lodge & Hutz LLP

(57) ABSTRACT

The invention proposes a fragrance dispenser, comprising a first and a second carrier, each carrier comprising one or more fragrance substances, wherein the fragrance substances comprise one or more fragrance substances a) with a vapor pressure of at least 0.1 mmHg at 25° C. ("HVA") and one or more fragrance substances b) with a vapor pressure of less than 0.1 mmHg at 25° C. ("LVA"), and wherein the fragrance substances are distributed to the first and second carrier such that at least 80 wt.-% of all HVA fragrance substances are carried by the first carrier.

17 Claims, 2 Drawing Sheets

HVA chamber covered with evaporation retardant barrier

LVA chamber – no evaporation retardant barrier

U.S. PATENT DOCUMENTS

| | | | |
|---|---|---|---|
| 3,954,964 A * | 5/1976 | Kuderna, Jr. | 512/4 |
| 4,094,119 A * | 6/1978 | Sullivan | 53/400 |
| 4,146,566 A | 3/1979 | Gaiser | |
| 4,233,161 A | 11/1980 | Sato et al. | |
| 4,356,969 A | 11/1982 | Obermayer et al. | |
| 4,590,111 A | 5/1986 | Takeuchi | |
| 4,603,030 A | 7/1986 | McCarthy | |
| 4,889,286 A * | 12/1989 | Spector | 239/47 |
| 5,342,584 A * | 8/1994 | Fritz et al. | 422/124 |
| 6,012,643 A | 1/2000 | Barlow et al. | |
| 6,063,365 A | 5/2000 | Shefer et al. | |
| 2006/0202050 A1* | 9/2006 | Caserta et al. | 239/34 |

FOREIGN PATENT DOCUMENTS

| | | | |
|---|---|---|---|
| EP | 1340513 | * | 9/2003 |
| EP | 1340513 A1 | | 9/2003 |
| EP | 1340513 A1 | * | 9/2003 |
| JP | H02-252462 | * | 11/1990 |

OTHER PUBLICATIONS

M.J. Saxby ed. "Food Taints and Off Flavors" ed. Saxby 1996 Blackie Academic and Professional, Suffolk UK p. 256.*

Limonene-Wikipedia (Limonene Wikipedia printed Sep. 24, 2011 Property Table) {http://en.wikipedia.org/wiki/Limonene}.*

Ethyl Vanillin—tradeindia (trade india.com; printed Sep. 24, 2011) {http://www.tradeindia.com/suppliers/ethyl-vanillin.html}.*

* cited by examiner

FRAGRANCE DISPENSER

CROSS REFERENCE TO RELATED APPLICATIONS

This application claims domestic priority benefits to International Application No. PCT/EP2007/051912, which was filed on Feb. 28, 2007, and published as WO 2008104226 A1 on Sept. 4, 2008, the entire content of each of which is hereby incorporated by reference.

The present invention describes a fragrance dispenser, particularly for use as an air-freshener system, with improved air-freshening properties compared to conventional air-freshener systems known to the art.

Air-freshener products are known to the art in a broad variety of product forms, each of them with specific profiles of advantages and disadvantages.

A common challenge of air-fresheners found in the market is that the more volatile components of a fragrance composition, particularly a perfume composition, evaporate faster than the less volatile components of the composition. This phenomenon often leads to a drastic shift of the fragrance composition and results in a noticeable olfactory profile change of the air-freshener product during its useful life. Especially citrus, fruity and other fresh perfume types suffer a dramatic change from fresh, citrus like smell at the beginning of product use to a more mellow smell of typical heart and base notes such as woody, musk and some heavy floral smells.

Faster evaporation of a fragrance composition's top note occurs due to its higher volatility. During usage of an e.g. conventional solid matrix air-freshener the top note will exhaust itself faster than the slower evaporating heart and bottom notes. The result is a significant composition change of the remaining fragrance composition, which leads to a pronounced change of olfactory character of the air-freshening product. This effect is undesirable since the consumer expects the product to maintain its olfactory character throughout the lifetime of the air-freshening product.

This leaves a need for fragrance dispenser with a significantly more constant odour profile through the life of the product.

U.S. Pat. No. 3,685,734 provides for a means of controlling the evaporation of a fragrance mixture with the benefit of obtaining a more constant fragrance emission rate than entirely open systems. It fails however to address the issue of the vast volatility differences in common fragrances with the result of having a changing fragrance character during the useful life of the product.

U.S. Pat. No. 4,356,969 describes a passive air freshener consisting of a fragrance reservoir and a touch protected surface membrane from which the fragrance can evaporate and provide a room fragrancing effect. While the surface area of the surface membrane and therefore overall fragrance emission rate per time unit can be varied the invention of this document does not address the evaporation speed differences of the constituents of common air-freshener fragrance compositions.

U.S. Pat. No. 4,590,111 discloses a fragrance releasing sheet article comprising a resin member with patterns and/or colours thereon and a fragrance releasing member comprising a resin and perfume, the pattern member and the fragrance releasing member being integrally constituted. improves on the appearance and flexibility in shape of conventional passive air-freshener systems with fragrance reservoir and evaporation regulating membrane. It does improve on the shortcoming of these systems in terms of their odour character change during use of the product. However, the character of the odour released during use of the sheet article still can easily change over time.

U.S. Pat. No. 6,012,643 relates to a device for controlled release of fragrant vapour in air. The device includes a carrier impregnated with a volatile medium and a wrapper of a flexible material surrounding said carrier for retaining the volatile medium on the carrier. The wrapper has a plurality of contiguous tear strips arranged in longitudinal sequence disposed over the carrier. The strips can be successively removed to expose a further portion of the carrier. The downside of this invention is the required consumer interaction with the product.

It was thus the object of the invention to provide improved fragrance dispensers and particularly air fresheners. The fragrance dispensers of the invention should secure a constant olfactory profile during the time of fragrance dispensation of the fragrance dispenser. The fragrance dispenser should also be easy to produce, it should allow to be produced in a variety of shapes, it should not require a user interaction after an initial activation of fragrance dispensation, and it should be useful for dispensing various fragrances, particularly fragrance compositions for air fresheners.

SUMMARY OF THE INVENTION

The invention thus provides a fragrance dispenser, comprising a first and a second carrier, each carrier comprising one or more fragrance substances, wherein the fragrance substances comprise one or more fragrance substances a) with a vapour pressure of at least 0.1 mmHg at 25° C. ("HVA") and one or more fragrance substances b) with a vapour pressure of less than 0.1 mmHg at 25° C. ("LVA"), and wherein the fragrance substances are distributed to the first and second carrier such that at least 80 wt.-% of all HVA fragrance substances are carried by the first carrier.

The invention is characterized by the following main areas of technical detail:
a) Definition of high volatility accord fragrance substances and low volatility accord fragrance substances,
b) provision of substantially separate carriers for HVA and LVA carriers, and
c) nature and technical specifications of a HVA evaporation retardant system (diffusion barrier).

Particularly, none of the above given prior art suggest to substantially separate carriers for HVA and LVA fragrance substances.

DETAILED DESCRIPTION OF THE INVENTION

Figure 1:
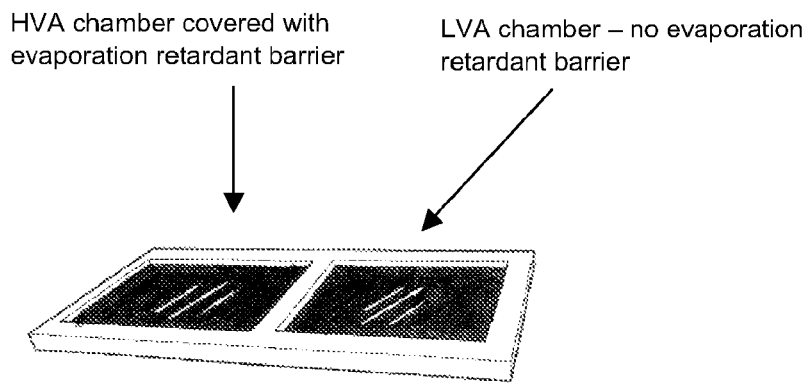
FIG. 1: Depicts a fragrance dispenser having an HVA chamber covered with an evaporation retardant barrier and an LVA chamber with no evaporation retardant burner.

Within the terms of the present invention, a fragrance dispenser is a device capable of and intended to dispense one or more fragrant substances ("fragrances") stored in a reservoir or in/on a carrier into air, optionally after an initial activation of the fragrance dispenser e. g. by removing or punctuating a fragrance vapour tight packaging. An air freshener within the terms of the present invention is a fragrance dispenser comprising a fragrance composition for eliciting a "fresh air smell", such smells being typically described by a perfumer by the attributes citrus, fruity or other fresh perfume type. The fragrance dispensers of the present invention are preferably "passive" fragrance dispensers or air fresheners, dispensing fragrances essentially at ambient temperatures, in contrast to "active" fragrance dispensers operating by heating fragrance reservoirs or carriers or fanning air over fragrance reservoirs or carriers by a ventilator. Unless stated otherwise, all descriptions hereinafter of a fragrance dispenser shall likewise disclose corresponding air fresheners and vice versa.

Fragrances are, according to the present invention, divided by their vapour pressure at 25° C. A high volatility accord ("HVA") fragrance substance is a substance having a vapour pressure of at least 0.1 mmHg at 25° C. and preferably not more than 100 mmHg. A low volatility accord ("LVA") fragrance substance is a substance having a vapour pressure of less than 0.1 mmHg at 25° C. Substances can be pure chemical substances or compositions comprising different chemical substances.

Typically, air-fresheners comprise fragrance substances having vapour pressures from about 0.001 mmHg at 25° C. to about 100 mmHg at 25° C., therefore spanning a factor of about 100000.

It has been found that fragrance and aroma chemicals and non-odoriferous compounds (solvents) with a vapour pressure ranging from 0.1 mmHg at 25° C. to 100 mmHg at 25° C. are particularly volatile and are rapidly lost by evaporation from an open matrix air-freshener operated at ambient temperature. It has furthermore been found that by physically separating HVA and LVA fragrance substances, fragrance substance carriers specially tailored for the dispensation of HVA and LVA fragrance substances, respective, can be employed.

The invention allows to make use of this insight by allowing to provide HVA and LVA fragrance substances on substantially separate carriers for fragrance substances, each of which can be specially adapted to the dispensation requirements of the fragrances comprised thereon. In all fragrance dispensers of the present invention, HVA and LVA fragrances are, optionally after activation of the fragrance dispenser, dispensed so that they can be simultaneously presented to the nose of a user or consumer, so that a scent provided by the fragrance dispenser comprises both HVA and LVA fragrance notes. The invention thus obviates the need of known air fresheners for a one-fits-all carrier of fragrance substances. Instead, the invention enables the skilled person to chose carriers particularly adapted to one another and to the fragrance substances such that the olfactory profile of the dispensed fragrances remains substantially constant during the lifetime (i.e. time of usefulness) of the fragrance dispenser.

It has also been found that the presence of a small amount of LVA fragrance substances on the first carrier and a small amount of HVA fragrance substances on the second carrier can be tolerated in view of the steadyness of the olfactory profile created by the fragrance dispenser. Thus, according to the invention the fragrance substances are distributed to the first and second carrier such that at least 80 wt.-%, preferably at least 90 wt.-%, more preferably at least 95 wt.-% and preferably all HVA fragrance substances are carried by the first carrier. This way, substantially all HVA fragrance substances are concentrated on the first carrier and make use of this carrier's advantageous properties for fragrance dispensation. Likewise, it is according to the invention preferred when the fragrance substances are distributed to the first and second carrier such that at least 80 wt.-%, preferably at least 90 wt.-%, more preferably at least 95 wt.-% and preferably all LVA fragrance substances are carried by the second carrier. In each case, it is preferred that the percentages of distribution apply to the moment when charging the first and second carrier with fragrance substances has been completed. Typically, the fragrance dispenser of the invention is sealed shortly after this moment, such that the distribution percentages do not change significantly, i.e. by more than 5 wt.-%, from the above values. A consumer would then remove the sealing, thus allowing the fragrances to be dispersed from their respective carriers (see below).

The HVA and LVA fragrances can be present in the fragrance dispenser of the invention in a variety of weight ratios. Preferably, the weight ratio of all HVA fragrance substances to all LVA fragrance substances of the first and second carrier is from 90:10 to 10:90, more preferably from 70:30 to 30:70, and most preferably from 60:40 to 40:60.

Preferred LVA fragrance substances are selected from the group consisting of Cinammic Alcohol (3-phenyl-2-propen-1-ol), Phenoxyethylalcohol (2-phenoxy ethanol), Undecavertol (4-methyl-3-decen-5-ol), Geraniol Supra (3,7-dimethyl-2,6-octadien-1-ol), Ethyl Linalool(3,7-dimethyl-1,6-nonadien-3-ol), Tetrahydrogeraniol (3,7-dimethyl-1-octanol), Genaryl Acetate Pure (3,7-dimethyl-2,6-octadien-1-yl-acetate), Terpineol Alpha (1-methyl-4-isopropyl-1-cyclo-hexen-8-ol), Isoborneol (exo-1,7,7-trimethyl-bicyclo (2.2.1)hepta-2-ol), Aldehyde C12 MNA (Methyl nonyl acetaldehyde), Aldehyde C11 (Undecenal), Terpinyl Acetate (2-(methyl-3-cyclohexenyl)-2-propyl-acetate), Undecylenic Aldehyde (10-undecylen-1-al), Agrunitril (3,7-dimethyl-6-octen-1-nitrile), Agrumex HC (2-tert.-butyl-cyclohexyl-acetate), Oryclon Special (4-tert.-butyl-cyclohexyl-acetate), Methyl Octin Carbonate (Methyl 2-nonynoate), Vanillin (3-methoxy-4-hydroxybenzaldehyde), Ethyl Vanillin (3-ethoxy-4-hydroxy-benzaldehyde), Galaxolide (Hexahydro-4,6,6,7,8,8-hexamethyl-cyclopenta-gamma-2-benzopyran), Iso E Super (2-acetyl-1,2,3,4,5,6,7,8-octahydro-2,3,8, 8-tetramethyl-naphtalene), Globalide (Oxacyclohexadecen-2-one), Geranyl Acetate (3,7-dimethyl-2,6-octadien-1-yl-acetate), Dimethyl Anthranilate (methyl n-methyl-anthranilate), Hydroherbaflorat/Corps 553 (tricyclo-decyl-acetate), Ethyl Safranate (ethyl dehydro cyclogeranate), 2-phenylethyl-dimethyl-carbinol, Geranyl Nitrile (3,7-dimethyl-2,6-octadien-1-nitrile), Phenyl Propyl Alcohol (3-phenyl-1-propanol), Hydroxycitronellal (3,7-dimethyl-7-hydroxyoctanal), methyl cinnamic aldehyde alpha, Nerol 900 (cis-3,7-dimethyl-2,6-octadien-1-ol), 9-decen-1-ol, Lilial (4-tert.-butyl-alpha-methyl-hydrocinnamic-aldehyde), Hedione (methyl-(2-pentyl-3-oxo-1-cyclo-pentyl)-acetate), Cyclamenaldehyde (2-methyl-3-(4-isopropylphenyl)-propanal), Florazon (3-(4-Ethylphenyl)-2,2-dimethylpropanal), Citronellol (3,7-dimethyl-6-octen-1-ol), Dipropylene Glycol (oxybispropanol), Diethyl Phthalate (1,2-benzenedicarboxylic acid diethyl ester), Isopropyl Myristate (1-methylethyl tetradecanoate), Dowanol TPM (Tripropylene Glycol Monomethyl Ether) and mixtures thereof.

Preferred HVA fragrance substances are selected from the group consisting of Anisic Aldehyde (4-methoxy-benzaldehyde), Orivone (4-tert.-pentyl-cyclohexanone), Phenylacetaldehyde Dimethyl Methyl Acetal (Phenyl-ethanal-dimethyl-acetal), Jasmaprunat (Ethyl-2-methyl-1,3-dioxolane-2-acetate), Allyl Amyl Glycolate, Anethol NPU 21/22 Celsius (1-methoxy-4-propenyl-benzene), Aldehyde C10 (1-decanal), Benzyl Acetate, Herboxan (2-butyl-4,4,6-trimethyl-1,3-dioxane), Leafovert (Cis-3-hexenyl-methyl-carbonate), Estragole (Basil Oil Fract.(Ocimum Basilicum L.)), Allyl Heptoate (2-propenyl-heptanoate), Vertocitral (2,4- And 3,5-dimethyl-3-cyclo-hexene-1-carboxaldehyde), Freesiol/Corps 119 (2,6-dimethyl-heptan-2-ol), Aldehyde C9 (1-nonanal), Cis-3-Hexenol, Allyl Caproate (2-propenyl-hexanoate), Melonal (2,6-dimethyl-5-heptenal), Hexenyl Acetate Cis-3 (Cis-3-hexenyl Acetate), Ethyl Caproate (Ethyl Hexanoate), Hexyl Acetate, Manzanate (Ethyl-2-methyl-pentanoate), Prenyl Acetate (3-methyl-2-butenyl-acetate), Ethyl-2-Methyl Butyrate, Isoamyl Acetate (3-methyl-butyl-acetate), Isododecane (C12-isoparaffines), Dowanol PNP (Propylene Glycol N-propyl Ether), Ethyl Isobutyrate, Phenyl-ethanal, Oxane (1,3-Oxathiane, 2-methyl-4-propyl-, cis-), Vertocitral (2,4- and 3,5-dimethyl-3-cyclo-hexene-1-carboxaldehyde), Allyl Heptoate (2-propenyl-heptanoate), Rose Oxide (4-methyl-2-(2-methylpropen-1-yl) -tetrahydropyrane), Citronellal (3,7-dimethyl-6-octen-1-al), Butyl Acetate, Isoamyl Butyrate (3-methyl-butyl-butyrate), Filbertone (5-methyl-2-hepten-4-one), Isononyl Aldehyde, 2-Octanone, Cis-3-Hexenol, D-Limonene (1-methyl-4-(1-methylethenyl)-xyclohexene), Butyl Butyrate, Cresyl Methyl Ether Para (1-methoxy-4-methyl-benzene), Cyclohexyl Acetate, Ethyl Heptoate, Heptyl Acetate, Tetrahydrocitral (3,7-dimethyl-1-octanal), Tetrahydro Myrcenol (2,6-dimethyl-2-octanol), Frutinat (1,3-dimethyl-butyl-2-butenoate), Methyl Benzoate, Amarocit (1,1-dimethoxy-2,2,5-trimethyl-4-hexene), Herbac (3,3-dimethyl cyclohexyl methylketone), Neononyl Acetate (3,5,5-trimethyl hexyl acetate), Hexenyl Isobutyrate Cis Trans-3 (3-hexen-1-yl-isobutyrate), Geranyl Methyl Ether (3,7-dimethyl-2,6-octadien-1-methoxy), Methyl Acetophenone Para (1-methyl-4-acetyl-benzene), Dowanol DPM (Dipropylenglycol Monomethyl Ether), and mixtures thereof.

In particularly preferred fragrance dispensers of the invention, the first carrier comprises a diffusion barrier having a benzyl acetate vapour transmission rate of at most 1 g/(5 cm$^2$·24 h) at 25° C. The benzyl acetate vapour transmission rate can be measured by tightly covering a glass container half filled with benzyl acetate with the diffusion barrier to be tested, preferably a polymer film, and measuring the benzyl acetate weight loss over time while storing the container in a room which is conditioned at 25° C. The measured weight loss can then be standardized to the benzyl acetate vapour transmission per 24 hours through a 5 cm$^2$ sized diffusion barrier, preferably a polymer film, at 25° C. Particularly preferred is a benzyl acetate vapour transmission rate of more than 0.02 g per 24 hours through a 5 cm$^2$ sized diffusion barrier and less than 1.0 g per 24 hours through a 5 cm$^2$ sized diffusion barrier. Preferably, the benzyl acetate vapour transmission rate falls in the range of more than 0.05 g per 24 hours through a 5 cm$^2$ sized diffusion barrier and less than 0.5 g per 24 hours through a 5 cm$^2$ sized diffusion barrier.

By careful choice of the diffusion barrier material and thickness, the HVA fragrance substances' emission rate can be adjusted to match the emission rate of the LVA fragrance substances. It has been found that optimal fragrance performance can be realized by combining a freely evaporating LVA with a diffusion barrier enclosed HVA.

Preferred diffusion barriers are polymer films. While low density qualities of polyethylene or polypropylene or ethyl vinyl acetate and mixtures are preferred diffusion barrier, any other polymer could be used, given that it provides for appropriate fragrance permeability.

It has been found that the combination of the freely evaporating low volatility accord and the evaporation speed reduced high volatility accord will provide for an air freshening effect with much less odour character change over time than a corresponding conventional air freshener system with all fragrance substances evaporating out of one single phase.

Fragrance carriers of a fragrance dispenser of the present invention are materials or bodies capable of storing otherwise solid, liquid or gaseous fragrances, preferably by absorption or adsorption, and further capable of releasing the fragrances to air.

Preferably, the fragrance substances are attached to their respective carrier by absorbing them into appropriate porous substrates or are dispersed throughout a solid or semisolid gel network. Appropriate porous substrates can be chosen from, but are not limited to paper and/or cardboard, liquid absorbing fabrics, nonwoven fabrics, absorbing porous polymers such as polyethylene or polypropylene, porous minerals such as clay, bentonite, zeolite or spray dried sodium sulfate (Light Sulfate), or any other sufficiently inert material capable of absorbing more than its own weight in fragrance liquid, i.e. a composition comprising one ore more fragrance substances and optionally a solvent or dispersion liquid. Particularly, the carrier of LVA fragrance substances can be a hydrous or anhydrous gel network realized by suitable thickeners. Suitable thickeners are, but are not limited to, calcium stearate, aluminium stearate, sodium stearate, polyacrylate based polymers, polyacrylamide, polyamide derivatives, carboxymethylcellulose, polysaccharide based polymers such as carrageenan, Agar, Gellan Gum, Alginate or Xanthan Gum, waxes such as paraffin wax, petrolatum, silicas, long chain alcohols such as C8-C20 alcohols, particularly octadecyl alcohol, and long chain organic acids such as C8-C20 carboxylic acids, particularly octadecanoic acid.

Preferred LVA and HVA carrier combinations are:

| | LVA Carrier | HVA Carrier |
|---|---|---|
| a) | absorbent pad (e.g. cellulose) | gelled fragrance (e.g. silica) |
| b) | absorbent pad (e.g. cellulose) | liquid fragrance (wick evaporation) |
| c) | gelled fragrance (e.g. silica) | liquid fragrance (wick evaporation) |
| d) | aqueous gelled fragrance (e.g. carrageenan) | gelled fragrance (e.g. silica) |
| e) | aqueous gelled fragrance (e.g. carrageenan) | absorbent pad (e.g. cellulose) |
| f) | aqueous gelled fragrance (e.g. carrageenan) | liquid fragrance (wick evaporation) |

Only the compartment containing the HVA should be equipped with a diffusion barrier while the LVA containing compartment can be left open or covered with a protection film or net which does not influence the evaporation rate of the LVA fragrance substances.

The first and second carriers are separate from one another such that blending of HVA and LVA fragrance substances is essentially minimized. In particularly preferred fragrance dispensers of the present invention, there is no liquid flow connection between the first and second carrier. When LVA and HVA are in very close contact glass, metal (such as aluminum) or very low diffusion polymer barriers are preferably used to separate LVA and HVA and thereby prevent premature blending of LVA and HVA fragrance substances.

Preferably, the first and second carriers are held together by a frame. Within the scope of the present invention, a frame is a structure physically establishing and maintaining an attachment contact between the first and second carrier. Particularly preferred frames for connecting the first and second carrier are ropes or lines, base plates, connecting layers, moulded frames and housings.

Another preferred execution of the invention is comprised of two reservoirs separately comprising liquid LVA and liquid HVA constituents. Both containers are closed with the exception of a first and second carrier, preferably in the form of an absorbent fleece or wick reaching into the liquid containers but also extending outside the liquid container. Capillary action of the wick/fleece carriers allows the fragrance oil to diffuse through the wick/fleece wetting the entire wick/fleece including the portion outside the container. For the purpose of this invention the wick/fleece reaching into the HVA container is preferably outfitted with the required evaporation retarding barrier to realize a slowed down evaporation of HVA. The wick/fleece reaching into the LVA container is left open to allow the LVA to evaporate freely into the ambient air.

The following examples and figures are meant to describe preferred embodiments of the invention more closely, without limiting the scope of the claims.

EXAMPLE 1

A preferred fragrance dispenser of the invention as depicted in FIG. 1 comprises a molded frame composed of glass or metal, or diffusion tight plastics such as polyethylene terephthalate (PET) and PET copolymers or polyvinylidene chloride or other sufficiently diffusion tight and inert materials. The frame comprises two compartments holding the LVA substances carried on a second carrier in one compartment and the HVA substances carried on a first carrier in another compartment. The outer frame construction physically joins the two compartments as one product. The HVA containing compartment is covered with an evaporation retardant diffusion barrier film of polyethylene, e. g. low density polyethylene, or polypropylene, e. g. low density polypropylene, or ethyl vinyl acetate or mixtures thereof. The LVA containing compartment can be covered with a net or perforated polymer film in order to prevent consumer's direct contact with the fragrance, but not to hinder the LVA evaporation.

To prevent premature fragrance emission the fragrance dispenser preferably is packaged in a fragrance vapour tight outer packaging such as polyethylene terephthalate (PET) or polyvinylidene chloride. Preferably, both first and second carrier are separately or together covered with a vapour tight film. Preferred vapour tight films comprise metal foil such as aluminium, or polyethylene terephthalate (PET), or polyvinylidene chloride or composites thereof. The consumer activates the product by removing (peeling off) the vapour tight film(s), while the evaporation retardant diffusion barrier covering the HVA compartment and an optional perforated protective layer covering the LVA compartment remain covering the compartments. A fragrance vapour tight outer packaging can be generally provided for all fragrance dispensers of the present invention, as described above.

EXAMPLE 2

Figure 2:
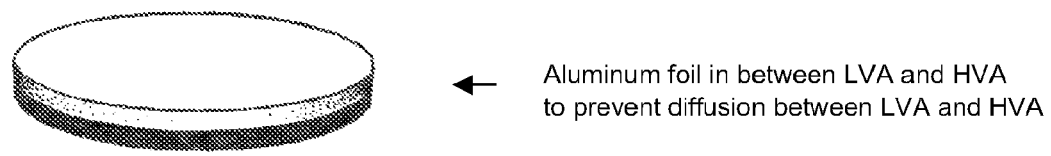
FIG. 2: Depicts a fragrance dispenser having aluminum foil in between the LVA and the HVA to prevent diffusion between the LVA and the HVA.

Another preferred and very cost effective embodiment of the invention comprises two absorbent cellulose based pads, one of which is charged with LVA and the other same sized pad is charged with HVA. The HVA containing pad is coated with a species of the earlier described evaporation retardant polymer foil while the other cellulose pad is left uncovered. In a three layer sandwich configuration (cf. FIG. 2) the two fragrance containing pads are joined using appropriate adhesive material with a diffusion barrier consisting of metal foil (such as aluminum foil) in between the fragranced pads. In use the air freshening device is kept in upright position by a simple stand holding the device upright or it can be hung, ensuring that both surfaces are allowed to emit fragrance freely.

To prevent premature fragrance emission the air-freshener device should be packaged in a fragrance vapour tight outer packaging, as described e. g. in example 1.

EXAMPLE 3

Figure 3:
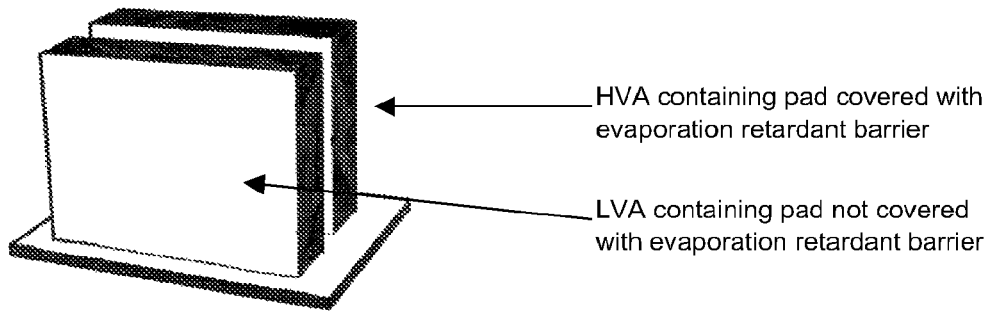
FIG. 3: Depicts a fragrance dispenser having two absorbent cellulose based pads, one of which is charged with LVA and the other same sized pad is charged with HVA; the pad charged with HVA is covered with an evaporation retardant barrier.

Another preferred embodiment of the invention (cf. FIG. 3) comprises two absorbent cellulose based pads, one of which is charged with LVA and the other same sized pad is charged with HVA. The HVA containing pad is coated with a species of the earlier described evaporation retardant polymer foil while the other cellulose pad is left uncovered. Both absorbent pads are mounted on a suitable stand composed of glass, or metal, or diffusion tight plastics such as polyethylene terephthalate (PET) and PET copolymers or polyvinylidene chloride or other sufficiently diffusion tight and inert materials. The mounting stand is configured in such a manner that the fragrance charged pads do not have physical contact.

To prevent premature fragrance emission the air-freshener device should be packaged in a fragrance vapour tight outer packaging, e. g. as described in example 1.

EXAMPLE 4

Figure 4:
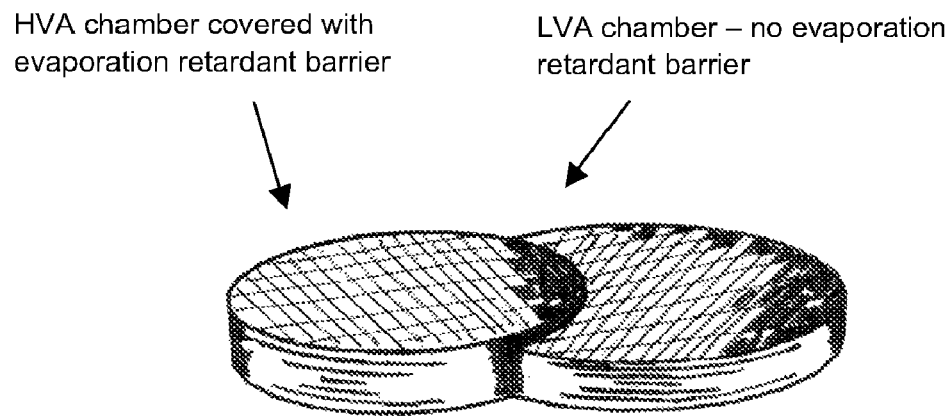
FIG. 4: Depicts a fragrance dispenser having two fragrance carriers, one located in a HVA compartment and the other located in an adjacent LVA compartment.

Another preferred embodiment of the present invention (cf. FIG. 4) comprises again two fragrance carriers, one located in a HVA compartment and the other located in an adjacent LVA compartment. The HVA compartment is outfitted with a diffusion barrier as described in Examples 1-3. Additionally, both compartments are covered with a fragrance vapour tight foil e. g. as described in example 1. Both vapour tight foils will be removed by the consumer to activate the product. The diffusion barrier remains on the HVA compartment to restrict evaporation and dispensation of the HVA fragrance substances.

EXAMPLE 5

Figure 5:
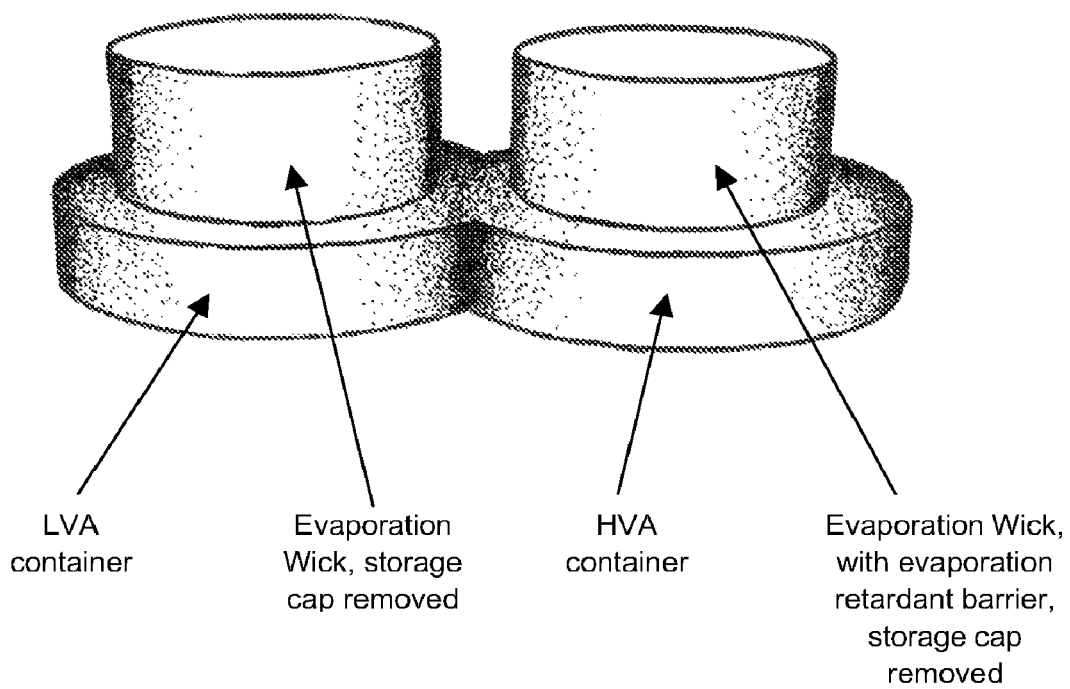
FIG. 5: Depicts a fragrance dispenser having two fragrance containers, one filled with the LVA in liquid form and the other one filled with the HVA in liquid form. Both containers are physically attached to each other but are individually outfitted with an absorbing wick reaching into liquids of the respective containers while also extending outside the liquid container.

Another preferred embodiment of the invention (cf. FIG. 5) comprises of 2 separate containers, one filled with the LVA in liquid form and the other one filled with the HVA in liquid form. Both containers are physically attached to each other. Each container is outfitted with an absorbing wick reaching into liquids of the respective containers while also extending outside the liquid container. The outside part of the wick reaching into the HVA container is outfitted with an evaporation retardant polymer foil, while the wick reaching into the LVA container is left uncovered. To prevent premature fragrance emission both wicks are covered with caps of fragrance vapour tight materials such as polyethylene terephthalate (PET) or polyvinylidene chloride or metal lined polymers or other fragrance vapour tight outer packaging as described in example 1. In order to activate the air-freshening device the consumer removes by e.g. unscrewing the two wick covering caps.

Performance Testing and Weight Loss

A typical air-freshener fragrance of the fruity family was chosen. All fragrance components of the composition were listed with ascending vapour pressure. All fragrance constituents with vapour pressure value below 0.1 mmHg were attributed to the LVA while all fragrance materials with vapour pressure higher than 0.1 mmHG became part of the HVA.

All three fragrances (complete fragrance, HVA and LVA) were applied onto typical cardboard air-freshener substrates. 6 grams of the complete fragrance were applied onto a 5 cm×10 cm sized cardboard piece while 2.86 g of the LVA was applied onto a 5 cm×5 cm sized cardboard piece and 3.14 g of the HVA was applied onto a 5 cm×5 cm sized cardboard piece. The cardboards with the complete fragrance and the LVA were left to evaporate in a large room conditioned at temperature between 20 and 25° C. The HVA charged cardboard was heat-sealed in a PE polymer foil with the polymer weighing 0.22 g. The sealed HVA charged cardboard was left to evaporate in the same room as the complete fragrance and LVA charged cardboards. Throughout a period of 17 days the weight loss of all three fragrance charged cardboards was determined gravimetrically and recorded.

In order to evaluate the products air-freshening quality the cardboards were placed in 4 m$^3$ sized evaluation booths and left for 1 h to evaporate into the closed booths. This test was performed at days 1, 3, 4, 5, 6, 7, 10, 12, 17 of the testing period. The HVA and LVA containing cardboards were placed in the same evaluation booth, while the complete fragrance containing cardboard was placed in a separate evaluation booth.

Strength and quality of the fragrance impression in the evaluation booths were evaluated by trained fragrance evaluators. (Evaluation scales: Strength 0=no smell, Strength 10=extremely strong smell; Quality 0=Totally different smell from fragrance character emitted from freshly prepared product, Quality 10=Fragrance character identical to character emitted from freshly prepared product.

Test Fragrances

The following table shows a composition of a typical air-freshener fragrance of the fruity family. The vapour pressure of each constituent was calculated by the software program "EpiWin" of Howard+Meylan. In the table these calculated vapour pressures are stated as the decadic logarithm of the calculated vapour pressure in mmHg at 25° C. For the purpose of separating the fragrance in HVA and LVA all fragrance constituents with log(vapour pressure) equal or greater than −1 became part of the HVA and all fragrance constituents with log (vapour pressure) less than −1 became part of the LVA.

When separating the complete fragrance into HVA and LVA the quantitative proportions between the individual constituents were kept as in the complete fragrance.

Complete Fragrance "Fruity Freshener"

| Trade Name | Chemical Name | Parts | log (vapour pressure) |
|---|---|---|---|
| Agrumex LC | 2-TERT.-BUTYL-CYCLOHEXYL-ACETATE | 8.00 | −1.16 |
| Allyl Heptoate | 2-PROPENYL-HEPTANOATE | 2.50 | −0.64 |
| Benzyl Acetate | BENZYL-ACETATE | 15.00 | −0.79 |
| Calone 1951 | 7-METHYL-3,4-DIHYDRO 2H-1,5-BENZODIOXEPINE-3-ONE | 0.20 | −3.14 |
| Citral 95 | 3,7-DIMETHYL-2,6-OCTADIENAL | 0.60 | −0.83 |
| Coumarin | 5,6-BENZO-ALPHA-PYRONE | 0.60 | −2.57 |
| Damascone Delta | 1-(2,6,6-TRIMETHYL-3-CYCLOHEXEN-1-YL)-2-BUTEN-1-ONE | 0.40 | −1.57 |
| Decalactone Gamma | 4-DECANOLIDE | 1.00 | −2.29 |
| Ethyl Butyrate | ETHYL BUTYRATE | 0.20 | 1.08 |
| Ethyl Methyl Butyrate-2 | ETHYL-2-METHYL-BUTYRATE | 0.30 | 0.90 |
| Geranyl Acetate 60 | 3,7-DIMETHYL-2,6-OCTADIEN-1-YL-ACETATE | 2.00 | −1.54 |
| Heliotropin | 3,4-METHYLENEDIOXYBENZALDEHYDE | 0.60 | −2.02 |
| Hexenyl Acetate Cis-3 | CIS-3-HEXENYL ACETATE | 0.20 | 0.06 |
| Hexyl Acetate | HEXYL-ACETATE | 4.00 | 0.19 |
| Isoraldeine 70 | 4-(2,6,6-TRIMETHYL-2-CYCLOHEXENYL-)-3-METHYL-3-BUTEN-2-ONE | 1.50 | −2.01 |
| Lilial | 4-TERT.-BUTYL-ALPHA-METHYL-HYDROCINNAMIC-ALDEHYDE | 2.50 | −2.45 |
| Linalool | 3,7-DIMETHYL-1,6-OCTADIENE-3-OL | 11.00 | −1.24 |
| Manzanate | ETHYL-2-METHYL-PENTANOATE | 0.30 | 0.46 |
| Melonal | 2,6-DIMETHYL-5-HEPTENAL | 0.30 | −0.12 |
| Orange Oil Brazil | ORANGE OIL | 3.50 | 0.83 |
| Orivone | 4-TERT.-PENTYL-CYCLOHEXANONE | 0.50 | −0.92 |
| Phenylethyl Alcohol | 2-PHENYLETHYL ALCOHOL | 2.50 | −1.79 |
| Prenyl Acetate | 3-METHYL-2-BUTENYL-ACETATE | 4.00 | 0.62 |
| Rose Oxide Inactive | 4-METHYL-2-(2-METHYLPROPEN-1-YL)-TETRAHYDRO-PYRANE | 0.30 | −0.18 |
| Styralyl Acetate | 1-PHENYLETHYL-ACETATE | 4.00 | −1.02 |
| Vertocitral | 2,4- AND 3,5-DIMETHYL-3-CYCLOHEXENE-1-CARBOXALDEHYDE | 6.00 | −0.45 |

LVA of "Fruity Freshener"

| Trade Name | Chemical Name | Parts | log (vapour pressure) |
|---|---|---|---|
| Agrumex LC | 2-TERT.-BUTYL-CYCLOHEXYL-ACETATE | 8.00 | −1.16 |
| Calone 1951 | 7-METHYL-3,4-DIHYDRO 2H-1,5-BENZODIOXEPINE-3-ONE | 0.20 | −3.14 |
| Coumarin | 5,6-BENZO-ALPHA-PYRONE | 0.60 | −2.57 |
| Damascone Delta | 1-(2,6,6-TRIMETHYL-3-CYCLOHEXEN-1-YL)-2-BUTEN-1-ONE | 0.40 | −1.57 |
| Decalactone Gamma | 4-DECANOLIDE | 1.00 | −2.29 |
| Geranyl Acetate 60 | 3,7-DIMETHYL-2,6-OCTADIEN-1-YL-ACETATE | 2.00 | −1.54 |
| Heliotropin | 3,4-METHYLENEDIOXYBENZALDEHYDE | 0.60 | −2.02 |
| Isoraldeine 70 | 4-(2,6,6-TRIMETHYL-2-CYCLOHEXENYL-)-3-METHYL-3-BUTEN-2-ONE | 1.50 | −2.01 |
| Lilial | 4-TERT.-BUTYL-ALPHA-METHYL-HYDROCINNAMIC-ALDEHYDE | 2.50 | −2.45 |
| Linalool | 3,7-DIMETHYL-1,6-OCTADIENE-3-OL | 11.00 | −1.24 |
| Phenylethyl Alcohol | 2-PHENYLETHYL ALCOHOL | 2.50 | −1.79 |
| Styralyl Acetate | 1-PHENYLETHYL-ACETATE | 4.00 | −1.02 |

HVA of "Fruity Freshener"

| Trade Name | Chemical Name | Parts | log (vapour pressure) |
|---|---|---|---|
| Allyl Heptoate | 2-PROPENYL-HEPTANOATE | 2.50 | −0.64 |
| Benzyl Acetate | BENZYL-ACETATE | 15.00 | −0.79 |
| Citral 95 | 3,7-DIMETHYL-2,6-OCTADIENAL | 0.60 | −0.83 |
| Ethyl Butyrate | ETHYL BUTYRATE | 0.20 | 1.08 |
| Ethyl Methyl Butyrate-2 | ETHYL-2-METHYL-BUTYRATE | 0.30 | 0.90 |
| Hexenyl Acetate Cis-3 | CIS-3-HEXENYL ACETATE | 0.20 | 0.06 |
| Hexyl Acetate | HEXYL-ACETATE | 4.00 | 0.19 |
| Manzanate | ETHYL-2-METHYL-PENTANOATE | 0.30 | 0.46 |
| Melonal | 2,6-DIMETHYL-5-HEPTENAL | 0.30 | −0.12 |
| Orange Oil Brazil | ORANGE OIL | 3.50 | 0.83 |
| Orivone | 4-TERT.-PENTYL-CYCLOHEXANONE | 0.50 | −0.92 |
| Prenyl Acetate | 3-METHYL-2-BUTENYL-ACETATE | 4.00 | 0.62 |
| Rose Oxide Inactive | 4-METHYL-2-(2-METHYLPROPEN-1-YL)-TETRAHYDRO-PYRANE | 0.30 | −0.18 |
| Vertocitral | 2,4- AND 3,5-DIMETHYL-3-CYCLOHEXENE-1-CARBOXALDEHYDE | 6.00 | −0.45 |

Results
Weight Loss

| days of evaporation | LVA + HVA (no barrier) | LVA (no barrier) | HVA (with barrier) |
|---|---|---|---|
| | % fragrance left | | |
| 0.0 | 100.0% | 100.0% | 100.0% |
| 0.3 | 89.5% | 96.8% | 94.8% |
| 3.0 | 55.8% | 78.9% | 69.2% |
| 4.0 | 45.7% | 71.4% | 60.4% |
| 5.3 | 32.0% | 58.4% | 49.7% |
| 6.0 | 27.3% | 52.3% | 44.8% |
| 7.1 | 21.3% | 44.8% | 39.3% |
| 10.0 | 11.0% | 30.8% | 25.0% |
| 12.0 | 9.2% | 26.9% | 18.5% |
| 17.0 | 6.5% | 20.1% | 8.8% |

Air-Freshening Performance—Fragrance Strength in Test Booth

| days of evaporation | Complete fragrance "Fruity Freshener" (no barrier) | LVA and HVA separated (HVA with barrier) combined in test booth |
|---|---|---|
| | fragrance strength | |
| 0.0 | 8.2 | 7.0 |
| 0.3 | 7.0 | 6.8 |
| 3.0 | 5.8 | 6.7 |
| 4.0 | 5.4 | 6.5 |
| 5.3 | 5.4 | 6.4 |
| 6.0 | 4.6 | 6.2 |
| 7.1 | 4.4 | 5.4 |
| 10.0 | 4.0 | 5.0 |
| 12.0 | 3.1 | 4.1 |
| 17.0 | 1.6 | 1.8 |

Air-Freshening Performance—Truth to Original Fragrance Note

| days of evaporation | Complete fragrance "Fruity Freshener" (no barrier) truth to original fragrance | LVA and HVA separated (HVA with barrier) combined in test booth |
|---|---|---|
| 0.0 | 10.0 | 9.0 |
| 0.3 | 7.0 | 8.6 |
| 3.0 | 5.8 | 8.8 |
| 4.0 | 4.6 | 8.0 |
| 5.3 | 4.2 | 8.0 |
| 6.0 | 4.2 | 8.2 |
| 7.1 | 3.4 | 7.6 |
| 10.0 | 3.3 | 7.1 |
| 12.0 | 2.2 | 6.2 |
| 17.0 | 2.0 | 3.4 |

What is claimed is:

1. A passive fragrance dispenser for simultaneously presenting HVA (high volatility accord) and LVA (low volatility accord) fragrances, comprising a first and a second carrier, each carrier comprising one or more fragrance substances, wherein the fragrance substances comprise one or more fragrance substances a) with a vapor pressure of at least 0.1 mm Hg at 25° C. ("HVA") and one or more fragrance substances b) with a vapor pressure of less than 0.1 mm Hg at 25° C. ("LVA"), and wherein the fragrance substances are distributed to the first and second carrier such that at least 80 wt. % of all HVA fragrance substances are carried by the first carrier, and wherein the first carrier is covered by a diffusion barrier having a benzyl acetate vapour transmission rate of more than 0.02 and less than 1 g/(5 cm$^2$ ·24 h) at 25° C., and wherein the second carrier remains free of a diffusion barrier, further wherein the first and second carrier are separated from one another such that the total weight of LVA substances in the first carrier does not increase by more than 35 wt. % relative to the LVA content of the first carrier within 30 days after producing the fragrance dispenser.

2. The fragrance dispenser of claim 1, wherein the fragrance substances are distributed to the first and second carrier such that at least 80 wt % of all LVA fragrance substances are carried by the second carrier.

3. The fragrance dispenser of claim 1, wherein the weight ratio of all HVA fragrance substances to all LVA fragrance substances of the first and second carrier is from 90:10 to 10:90.

4. The fragrance dispenser of claim 1, wherein the one or more HVA fragrance substances are selected from the group consisting of Anisic Aldehyde (4-methoxy-benzaldehyde), Orivone (4-tert.-pentyl-cyclohexanone), Phenylacetaldehyde Dimethyl Methyl Acetal (Phenyl-ethanal-dimethyl-acetal), Jasmaprunat (Ethyl-2-methyl-1,3-dioxolane-2-acetate), Allyl Amyl Glycolate, Anethol NPU 21/22 Celsius (1-methoxy-4-propenyl-benzene), Aldehyde C10 (1-decanal), Benzyl Acetate, Herboxan (2-butyl-4,4,6-trimethyl-1,3-dioxane), Leafovert (Cis-3-hexenyl-methyl-carbonate), Estragole (Basil Oil Fract.(Ocimum Basilicum L.)), Allyl Heptoate (2-propenyl-heptanoate), Vertocitral (2,4- And 3,5-dimethyl-3-cyclo-hexene-1-carboxaldehyde), Freesiol/Corps 119 (2,6-dimethyl-heptan-2-ol), Aldehyde C9 (1-nonanal), Cis-3-Hexenol, Allyl Caproate (2-propenyl-hexanoate), Rose Oxide HC (4-methyl-2-(2-methylpropen-1-yl)-tetrahydropyrane), Melonal (2,6-dimethyl-5-heptenal), Hexenyl Acetate Cis-3 (Cis-3-hexenyl Acetate), Ethyl Caproate (Ethyl Hexanoate), Hexyl Acetate, Manzanate (Ethyl-2-methyl-pentanoate), Prenyl Acetate (3-methyl-2-butenyl-acetate), Ethyl-2-Methyl Butyrate, Isoamyl Acetate (3-methyl-butyl-acetate), Isododecane (C12-isoparaffines), Dowanol PNP (Propylene Glycol N-propyl Ether), Ethyl Isobutyrate, Phenyl-ethanal, Oxane (1,3-Oxathiane, 2-methyl-4-propyl-, cis-), Vertocitral (2,4- and 3,5-dimethyl-3-cyclo-hexene-1-carboxaldehyde), Allyl Heptoate (2-propenyl-heptanoate), Rose Oxide (4-methyl-2-(2-methylpropen-1-yl)-tetrahydropyrane), Citronellal (3,7-dimethyl-6-octen-1-al), Butyl Acetate, Isoamyl Butyrate (3-methyl-butyl-butyrate), Filbertone (5-methyl-2-hepten-4-one), Isononyl Aldehyde, 2-Octanone, Cis-3-Hexenol, D-Limonene (1-methyl-4-(1-methylethenyl)-xyclohexene), Butyl Butyrate, Cresyl Methyl Ether Para (1-methoxy-4-methyl-benzene), Cyclohexyl Acetate, Ethyl Heptoate, Heptyl Acetate, Tetrahydrocitral (3,7-dimethyl-1-octanal), Tetrahydro Myrcenol (2,6-dimethyl-2-octanol), Frutinat (1,3-dimethyl-butyl-2-butenoate), Methyl Benzoate, Amarocit (1,1-dimethoxy-2,2,5-trimethyl-4-hexene), Herbac (3,3-dimethyl cyclohexyl methylketone), Neononyl Acetate (3,5,5-trimethyl hexyl acetate), Hexenyl Isobutyrate Cis Trans-3 (3-hexen-1-yl-isobutyrate), Geranyl Methyl Ether (3,7-dimethyl-2,6-octadien-1-methoxy), Methyl Acetophenone Para (1-methyl-4-acetyl-benzene), and Dowanol DPM (Dipropylenglycol Monomethyl Ether), and mixtures thereof.

5. The fragrance dispenser of claim 1, wherein the one or more LVA fragrance substances are selected from the group consisting of Cinammic Alcohol (3-phenyl-2-propen-1-ol), Phenoxyethylalcohol (2-phenoxy ethanol), Undecavertol (4-methyl-3-decen-5-ol), Geraniol Supra (3,7-dimethyl-2,6-octadien-1-ol), Ethyl Linalool(3,7-dimethyl-1,6-nonadien-3-ol), Tetrahydrogeraniol (3,7-dimethyl-1-octanol), Genaryl Acetate Pure (3,7-dimethyl-2,6-octadien-1-yl-acetate), Terpineol Alpha (1-methyl-4-isopropyl-1-cyclo-hexen-8-ol), Isoborneol (exo-1,7,7-trimethyl-bicyclo(2.2.1)hepta-2-ol), Aldehyde C12 MNA (Methyl nonyl acetaldehyde), Aldehyde C11 (Undecenal), Terpinyl Acetate (2-(methyl-3-cyclohexenyl)-2-propyl-acetate), Undecylenic Aldehyde (10-undecylen-1-al), Agrunitril (3,7-dimethyl-6-octen-1-nitrile), Agrumex HC (2-tert.-butyl-cyclohexyl-acetate), Oryclon Special (4-tert.-butyl-cyclohexyl-acetate), Methyl Octin Carbonate (Methyl 2-nonynoate), Vanillin (3-methoxy-4-hydroxybenzaldehyde), Ethyl Vanillin (3-ethoxy-4-hydroxybenzaldehyde), Galaxolide (Hexahydro-4,6,6,7,8,8-hexamethyl-cyclopenta-gamma-2-benzopyran), Iso E Super (2-acetyl-1,2,3,4,5,6,7,8-octahydro-2,3,8,8-tetramethyl-naphtalene), Globalide (Oxacyclohexadecen-2-one), Geranyl Acetate (3,7-dimethyl-2,6-octadien-1-yl-acetate), Dimethyl Anthranilate (methyl n-methyl-anthranilate), Hydroherbaflorat/Corps 553 (tricyclo-decyl-acetate), Ethyl Safranate (ethyl dehydro cyclogeranate), 2-phenylethyl-dimethyl-carbinol, Geranyl Nitrile (3,7-dimethyl-2,6-octadien-1-nitrile), Phenyl Propyl Alcohol (3-phenyl-1-propanol), Hydroxycitronellal (3,7-dimethyl-7-hydroxyoctanal), methyl cinnamic aldehyde alpha, Nerol 900 (cis-3,7-dimethyl-2,6-octadien-1-ol), 9-decen-1-ol, Lilial (4-tert.-butyl-alpha-methyl-hydrocinnamic-aldehyde), Hedione (methyl-(2-pentyl-3-oxo-1-cyclo-pentyl)-acetate), Cyclamenaldehyde (2-methyl-3-(4-isopropylphenyl)-propanal), Florazon (3-(4-Ethylphenyl)-2,2-dimethylpropanol), Citronellol (3,7-dimethyl-6-octen-1-ol), Dipropylene Glycol (oxybispropanol), Diethyl Phthalate (1,2-benzenedicarboxylic acid diethyl ester), Isopropyl Myristate (1-methylethyl tetradecanoate), and Dowanol TPM (Tripropylene Glycol Monomethyl Ether), and mixtures thereof.

6. The fragrance dispenser of claim 1, wherein the first and second carrier are held to each other by a frame.

7. The fragrance dispenser of claim 1, wherein the first and second carrier are independently from one another selected from the group consisting of paper, cardboard, porous fabrics capable of absorbing liquids, nonwovens, porous polyethylene, porous polypropylene, porous minerals, and gels.

8. The fragrance dispenser of claim 1, wherein the fragrance substances are distributed to the first and second carrier such that at least 90 wt. % of all HVA fragrance substances are carried by the first carrier.

9. The fragrance dispenser of claim 1, wherein the fragrance substances are distributed to the first and second carrier such that at least 95 wt. % of all HVA fragrance substances are carried by the first carrier.

10. The fragrance dispenser of claim 1, wherein the fragrance substances are distributed to the first and second carrier such that at least 90 wt. % of all LVA fragrance substances are carried by the second carrier.

11. The fragrance dispenser of claim 1, wherein the fragrance substances are distributed to the first and second carrier such that at least 95 wt. % of all LVA fragrance substances are carried by the second carrier.

12. The fragrance dispenser of claim 1, wherein the weight ratio of all HVA fragrance substances to all LVA fragrance substances of the first and second carrier is from 70:30 to 30:70.

13. The fragrance dispenser of claim 1, wherein the weight ratio of all HVA fragrance substances to all LVA fragrance substances of the first and second carrier is from 60:40 to 40:60.

14. The fragrance dispenser of claim 1, wherein the first carrier comprises a diffusion barrier having a benzyl acetate vapour transmission rate of between $0.05 \text{ g}/(5 \text{ cm}^2 \cdot 24 \text{ h})$ to $0.5 \text{ g}/(5 \text{ cm}^2 \cdot 24 \text{ h})$.

15. The fragrance dispenser of claim 1, wherein the diffusion barrier comprises a polymer film.

16. The fragrance dispenser of claim 1, wherein the fragrance substances are attached to the first and second carriers by absorption into a porous substrate.

17. The fragrance dispenser of claim 1, wherein the fragrance substances are attached to the first and second carriers by dispersion throughout a solid or a semi-solid gel network.

* * * * *